United States Patent [19]

Spicola et al.

[11] Patent Number: 5,154,788

[45] Date of Patent: Oct. 13, 1992

[54] METHOD FABRICATING LOAD-BEARING COMPOSITES FREE FROM MICROBUCKLING DEFORMATION UP TO A PREDETERMINED LOAD

[75] Inventors: Francis C. Spicola, Portsmouth; Neil J. Dubois, Cranston, both of R.I.

[73] Assignee: The United States of America as represented by the Secretary of the Navy, Washington, D.C.

[21] Appl. No.: 725,717

[22] Filed: Jul. 3, 1991

[51] Int. Cl.$^5$ .......................................... B65H 81/00
[52] U.S. Cl. .................................... 156/174; 156/166; 156/169
[58] Field of Search ............... 156/166, 169, 172, 173, 156/174, 175, 425

[56] References Cited

U.S. PATENT DOCUMENTS 4,248,649  2/1981  Harrison et al. ................... 156/174

OTHER PUBLICATIONS

Timoshenko, Stephen P., "Theory of Elastic Stability", McGraw-Hill Book Co. New York, 1936, pp. 94-98.
Waas, A. M., et al, "A Mechanical Model for Elastic Fiber Microbuckling," Journal of Applied Mechanics, Mar. 1990, vol. 57, pp. 138-149.
Rosen, B. W. "Mechanics of Composite Strengthening," Fiber Composite Materials, American Society for Metals, 1965, pp. 37-75.
Spicola, F. C., et al, "An Algorithm for the Analaysis of Critical Stresses in Uni-Directional Fiber Laminates," The 1990 ASME Int'l Computers in Engr. Conf. & Exposition, Aug. 5-9, 1990, pp. 1-8.
Lubin, George "Handbook of Composites" Published by Van Nostrand Reinhold Company, Inc., 1982, pp. 550-556.
Department of Defense Publication No. MIL-HD-BK-17A, Jan. 1971, Entitled "Plastics for Aerospace Vehicles".
Chamis, C. C., et al., "Impact Resistance of Unidirectional Fiber Composites," Composite Materials: Testing and Design (Second Conference) ASTM STP497, American Society for Testing and Materials, 1972, pp. 324-349.

Primary Examiner—Jeff H. Aftergut
Attorney, Agent, or Firm—Michael J. McGowan; Prithvi C. Lall; Michael F. Oglo

[57] ABSTRACT

A continuous filament is selected from among a group of appropriate types of filaments, and selection of the filament length and the filament thickness is made as well. A matrix material is selected from a group of appropriate types of matrix materials. Filaments of the selected type, length and thickness are undirectionally imbedded in the selected matrix to provide a uniaxial continuously reinforced composite. The Young's modulus, $E_c$, and the shear modulus $G_c$, are calculated for the composite. Mathematical formulas are provided for calculation of upper and lower bounds of transverse stiffness, B. A mathematical formula is provided for calculation of critical comprehensive stress, $P_c$. Transverse stiffness, B, is involved as one of the factors in this formula. Either one or the other of the upper bound of B or the lower bound of B are alternatively applied in calculating $P_c$, depending upon a consideration related to the shape of a cross section of the structural member into which the composite is to be formed. If the shape of the outline of such cross section includes at least one angular break, then the lower bound of B is applied in calculating $P_c$. If the shape of the outline of such cross section is curvilinear in its entirety, then the upper bound of B is applied in calculating $P_c$. A structural member subjected to load values below $P_c$ will be free from load-induced microbuckling with a high degree of certainty.

20 Claims, 2 Drawing Sheets

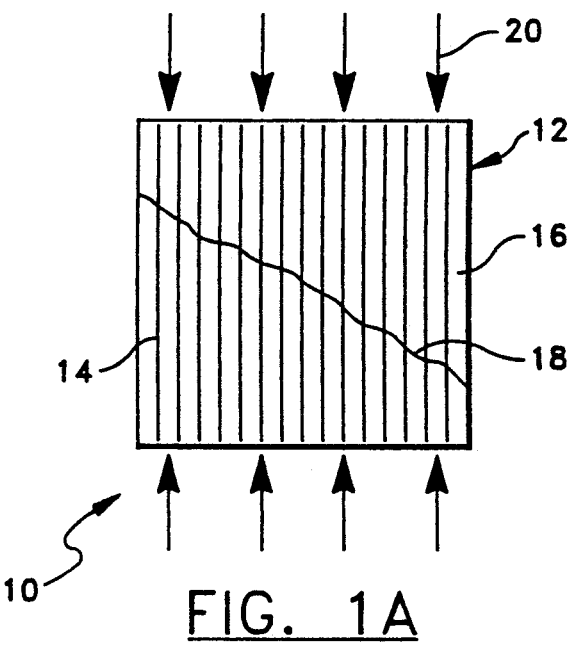
FIG. 1A
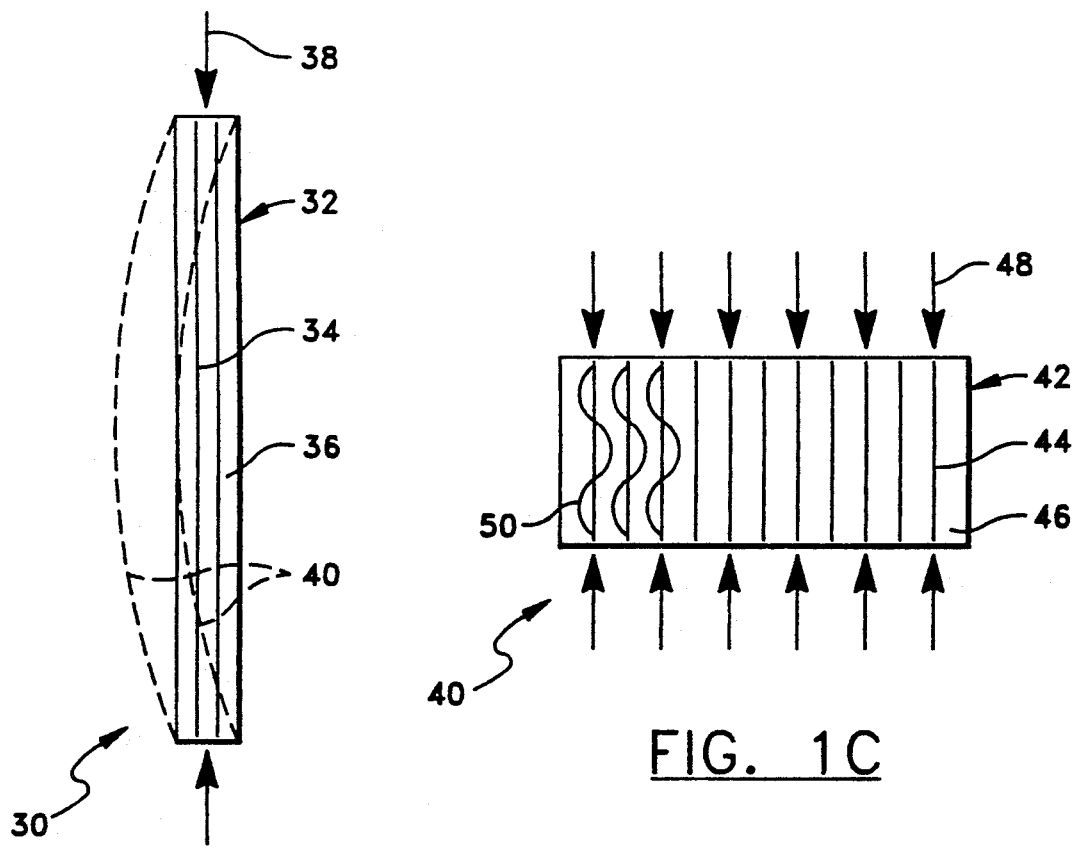
FIG. 1B
FIG. 1C

METHOD FABRICATING LOAD-BEARING COMPOSITES FREE FROM MICROBUCKLING DEFORMATION UP TO A PREDETERMINED LOAD

STATEMENT OF GOVERNMENT INTEREST

The present invention may be manufactured and used by or for the Government of the United States of America for governmental purposes without the payment of any royalties thereon or therefor.

BACKGROUND OF THE INVENTION

(1) Field of the Invention

The instant invention is drawn to the field of materials science, and more particularly, to a novel method of fabricating load-bearing reinforced composites that are free from microbuckling deformation up to a predetermined load.

(2) Description of the Prior Art

The heretofore known methods fabricating load-bearing reinforced composites were subject to poor quality control. The composites formed thereby deformed under loading at unexpected critical levels, which required that they be fabricated to be thicker than nominal by a "safety factor", with attendant materials wastage. Moreover, these "safety factors" were themselves in the nature of "guesstimates", insofar as such "safety factors" failed to take in account the way that the experimentally observed critical level at which microbuckling deformation occurred unexpectedly decreased with increased thickness of the reinforced composite, so that the heretofore known composites that were "thickened" by such "safety factors" were nonetheless subject to a lingering performance uncertainty which was not able to be gotten around. Reference in these connections may be had to a chapter entitled "Mechanics of Composite Strengthening" by B. W. Rosen, appearing in a book entitled, Fiber Composite Materials, (American Society for Metals, pp. 37-75, 1965), and to an article entitled "A Mechanical Model for Elastic Fiber Microbuckling", by A. M. Waas et al., appearing at Transactions of the ASME, Vol. 57, pp. 138-149, 1990, each incorporated herein in their entirety by reference.

A non-prior-art article (because its publication date was not more than one year prior to the application filing date hereof) to which reference is made is "An Algorithm for the Analysis of Critical Stresses in Unidirectional Continuous Fiber Laminates", by F. C. Spicola and N. J. Dubois, appearing at the Proceedings of the 1990 ASME International Computers in Engineering Conference and Exposition, August 5-9, Boston, Mass., Vol. 2, pp. 691-698. This article, which is authored by the present applicants, and which constitutes a disclosure generally coextensive with the present application, is also incorporated herein in its entirety by reference.

SUMMARY OF THE INVENTION

It is accordingly the principal object of the present invention to provide a method fabricating load-bearing reinforced composites that are free from loading-induced failure up to a predetermined load in accordance with which, and in a first step, continuous filaments are selected as reinforcing agents from the group comprising glass filaments, carbon filaments, and among others, KEVLAR filaments. In a second step, a medium is selected as a matrix from the group comprising epoxy, a thermoplastic, and among others, a thermosetting agent. In a next step, the filaments are uniformly embedded in spaced apart relation into the matrix to form a preselected uniaxial, continuous filament reinforced composite. In further accord therewith, and in a next step, the Young's modulus of elasticity of the preselected composite and the shear modulus of the preselected composite are calculated. In the preferred embodiment, a finite element analysis is disclosed to calculate these moduli. In further accord therewith, and in a next step, the transverse stiffness of the preselected composite is calculated using the calculated values for the Young's modulus and for the shear modulus of the preselected composite. Formulae for calculation of this variable for upper and a lower bounds thereof are disclosed, the lower bound being based upon an analysis for a corner continuous filament, and the upper bound being based upon an analysis for an edge continuous filament. The edge and corner uniaxially loaded continuous filaments are the ones that are first subject to failure. In further accord therewith, a critical load which may or may not include a predetermined safety factor, is calculated from the transverse stiffness value. With respect to load values below this critical load, the uniaxial continuous filament reinforced composite is free from load-induced microbuckling deformation with a high degree of certainty. Applicability of either the upper bound or lower bound as the actual failure bound is determined by the geometry of the composite component. A component whose cross section transverse to the direction of the filaments has a shape of outline including at least one angular break will fail at the lower bound. A component with a shape of outline of such cross section which is curvilinear in its entirety will fail at the upper bound.

BRIEF DESCRIPTION OF THE DRAWINGS

These and other features, advantages, and objects will become apparent to those skilled in the art upon reference to the following detailed description of the invention, and to the drawings, wherein:

FIG. 1 illustrates in FIGS. 1A, 1B, and 1C thereof diagrams useful in explaining the behavior of uniaxial continuous filament reinforced composites under loading;

DESCRIPTION OF THE PREFERRED EMBODIMENT

Figure 2A:
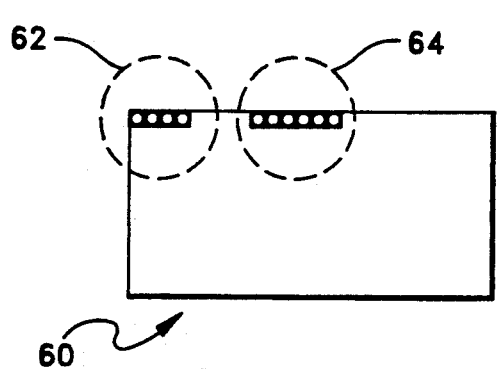
FIG. 2 illustrates in FIGS. 2A and 2B thereof diagrams useful in explaining the principles of the method for fabricating load-bearing reinforced composites that are free from load-induced microbuckling deformation up to a predetermined load of the present invention.

Continuous-fiber reinforced composites, such as those made from carbon, glass, epoxies reinforced by high molecular weight woven polyamids, thermoplastics, or thermosetting agents, among others, are subject to three modes of uniaxial compressive failure. ( A readily available form of high molecular weight woven polyamid is sold by the DuPont Company, under its trademark, KEVLAR.) In a first type, pure compressive failure, illustrated generally at 10 in FIG. 1A, a continuous fiber reinforced composite generally designated 12, constituted by continuous filaments 14 embedded in generally parallel and uniformly spaced relation within a matrix 16, tends to shear as illustrated by jagged line 18 when uniaxial compressive force illustrated by arrows 20 is applied thereto. The shear line 18, along which the composite is severed, destroys its mechanical integrity. This mode of failure is well understood, and is not further described herein.

In FIG. 1B, the second mode of load-induced deformation, global buckling, is generally designated at 30. This second mode typically occurs for uniaxially loaded continuous fiber reinforced composite aspect ratios of ten (10) or greater (length/width ratio), and in such manner that the continuous fiber reinforced composite generally designated 32, constituted as continuous, generally parallel filaments 34 uniformly embedded in spaced apart relation in a matrix 36, bows, as a whole, at some critical stress, illustrated by arrows 38, applied compressively thereto, which bow phenomenon is schematically illustrated in dashed outline 40. Like for the critical stress at which pure compressive failure occurs, the critical stress at which the phenomenon of global buckling occurs is well understood, and is not further described herein.

In FIG. 1C generally designated at 40 is a heuristical diagram illustrating the third failure mode, microbuckling, wherein a continuous fiber reinforced composite generally designated 42, constituted by continuous filaments 44 embedded in generally parallel uniform relation in a matrix 46, is subjected to a compressive load, P, schematically illustrated by arrows 48. The load 48 at some critical value, $P_c$, induces generally sinuous microbuckling of the filaments 44 of the continuous fiber reinforced composite 42, as schematically illustrated by waves 50. Although the waves 50 in FIG. 1C are solely diagrammatic, it is to be understood that through tests conducted on samples, in which load $P_c$ is applied, a nominal value for the wavelength of sinuous buckling is determined.

The relation between the critical load and the constitution of the uniaxial continuous fiber reinforced composite is described by the following relation:

$$P_c = \frac{n^2 E_f I_f}{L^2}\left[n^2 + \frac{BL^4}{n^2\pi^4 E_f I_f}\right] \qquad (1)$$

The relation (1) is well known as an energy conservation formula describing the buckling behavior of a beam on an elastic foundation subjected to uniaxial compressive loading, and reference may be made in this connection to "Theory of Elastic Stability" by Stephen P. Timoshenko and James M. Gere, published by McGraw-Hill Book Company, New York, N.Y., pp. 94–98 incorporated herein by reference. As applied in this context to the microbuckling of fibers, the parameters of relation (1) represent the following: n is the number of half-wavelengths of the waves 50 (FIG. 1C), $E_f$ is the Young's modulus of elasticity of the continuous fibers 44 (FIG. 1C), L is the length of the continuous fibers, B is the transverse stiffness of the composite, and $I_f$ is the moment of inertia of the continuous fibers 44 (FIG. 1C).

As appears more fully herein, novel relations are presented which allow the value of B to be calculated that accords with the experimentally observed behavior of continuous filament reinforced composites subjected to uniaxial loading, including the way that the critical stress decreases with increasing sample thickness, thereby allowing their fabrication in a manner to be described, that provides such composites that are free from loading induced microbuckling deformation up to a predetermined load with a high degree of certainty.

Referring now to FIG. 2A, generally designated at 60 is a plan view of a continuous fiber reinforced composite useful in explaining the principles of the present invention. The continuous fiber reinforced composite 60 is characterized by three sets of parameters, the modulus of elasticity for the composite, $E_c$, the shear modulus for the composite, $G_c$; the modulus of elasticity of the fiber, $E_f$, the shear modulus of the fiber, $G_f$, and the Young's modulus for the matrix, $E_m$, and the shear modulus for the matrix, $G_m$. In accord with the present invention, lower and upper bounds for the transverse stiffness respectively correspond to the behavior of corner continuous filaments, illustrated by a dashed circle 62, and to the behavior of edge continuous filaments, illustrated by a dashed circle 64. The processes for the calculations of the upper bound for transverse stiffness and of the lower bound for transverse stiffness will now be described, and in that order.

Figure 2B:
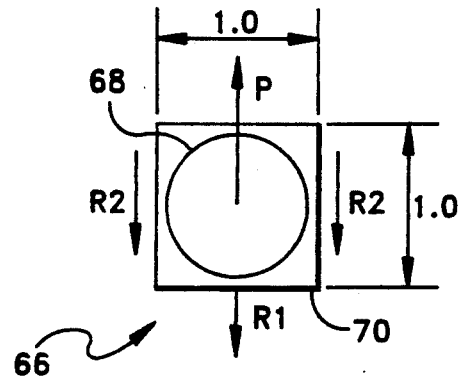

Referring now to FIG. 2B, generally designated at 66 is a diagram illustrating a fiber/matrix continuum cell located at the center of the outer layer of continuous filaments in the region 64 of FIG. 2A. The filament in the cell is designated at 68, and the matrix is designated at 70. The letter "P" represents the load, the indicia "$R_1$" represents normal reaction, and the indicia "$R_2$" represents shear reaction, which are related as follows:

$$\Sigma F_y = P - R_1 - 2R_2 = 0. \qquad (2)$$

$R_1$ and $R_2$ are related by normal and shear stiffness in the transverse plane. Thus, for the fiber/matrix continuum cell illustrated in FIG. 2B:

$$R_1 = \frac{E_c}{E_c + 4G_c} P \qquad (3)$$

and $$R_2 = \frac{2G_c}{E_c + 4G_c} P \qquad (4)$$

The variable $R_2$ does not vary with sample thickness, while the variable $R_1$ does, but shear stiffness has been effectively added to the overall stiffness of the elastic support through the weighting factor utilized in defining $R_1$ in terms of P.

As a result, the transverse stiffness B can be defined by $R_1$ only, and it varies with sample thickness.

Given that:

$$\delta = \frac{R_1 \frac{t}{2}}{AE_c} \qquad (5)$$

and substituting relation (3) into relation (5), $$\delta = \frac{\frac{E_c}{E_c + 4G_c} P \frac{t}{2}}{AE_c} \qquad (6)$$

where the displacement, $\delta$, is the deflection in the transverse direction to the direction of the stress load P.

For the normalized cell in FIG. 2B, for P=1 and for a cell area A=1, $$B = \delta^{-1} = \left[\frac{\frac{E_c}{E_c + 4G_c}\frac{t}{2}}{E_c}\right]^{-1} \quad (7)$$

where $E_c$ is the Young's modulus for the composite, $G_c$ is the shear modulus for the composite, and t is the test sample thickness in inches or in numbers of cells. During normalization, t is controlled by fiber diameter and fiber volume.

From equation (7), it can be readily seen that the transverse stiffness B decreases with increasing test sample thickness.

For the fibers at the corners of the outer layers where only half the shear support is realized, the relation describing the transverse stiffness is:

$$B = \delta^{-1} = \left[\frac{\frac{E_c}{E_c + 2G_c}\frac{t}{2}}{E_c}\right]^{-1} \quad (8)$$

In accordance with the present invention, equations (7) and (8) provide the upper and lower bounds, respectively, for the transverse shear stiffness, which is utilized in the equation (1) to calculate a range of critical loads below which continuous filament reinforced composites fabricated in a manner to be described are free from loading induced microbuckling deformation.

For a given continuous fiber reinforced composite, the values of $E_c$ and $G_c$ for the equations (7) and (8) are calculated in any suitable manner. In the preferred embodiment, a finite element analysis method is employed utilizing the following steps and parameters. A discretized mesh of the composite unit cell represented in FIG. 2B is constructed using plane strain elements. The area representing the fiber is assigned material properties of Young's modulus and shear modulus as have been experimentally measured for the particular fiber material being considered. Likewise material properties for the matrix portion of the unit cell are assigned to those elements. The finite element model is then subjected to two different loading conditions, one being uniaxial compression, the other being pure shear. The resulting deflections calculated yield values for the Young's modulus and shear modulus, respectively, of the composite.

Figure 3:
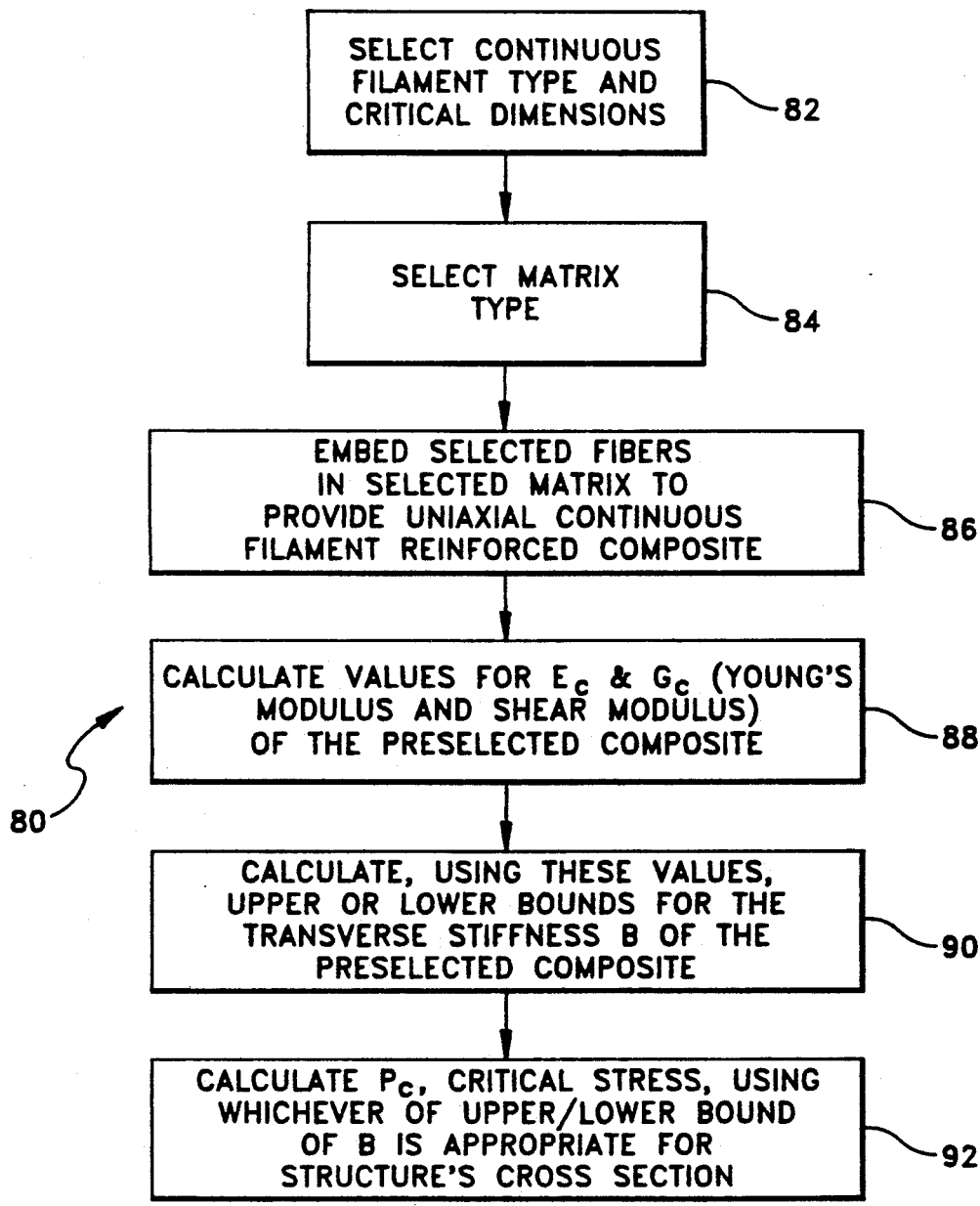
FIG. 3 is a process flow diagram illustrating the preferred embodiment of the method fabricating load-bearing reinforced composites that are free from load-induced microbuckling deformation up to a predetermined load in accord with the present invention.

Referring now to FIG. 3, generally designated at 80 is a process flow chart illustrating the presently preferred embodiment of the method fabricating load-bearing continuous filament reinforced composites that are free from deformation up to a predetermined load in accord with the present invention.

As shown by a block 82, and in a first step, the type and critical dimensions of the continuous filaments are selected. The filaments may be selected from the group comprising carbon, glass, and epoxy reinforced by high molecular weight woven polyamid (KEVLAR) filaments, among other continuous filaments well known to those skilled in the art, and the critical dimensions may be selected to include length, density and thickness of the continuous filaments.

As shown by a block 84, and in a next step, the matrix type is selected. The matrix type may be selected from the group comprising epoxies, thermoplastics, and thermosetting agents, among other matrix types well known to those skilled in the art. In a next step illustrated by a block 86, the selected continuous fibers are uniformly embedded in generally parallel relation into the selected matrix in such a way as to provide a preselected uniaxial, continuous filament reinforced composite. The embedding may occur by any method known to those skilled in the art, including the wet winding of a uniaxial composite in a cylindrical mandrel, wherein the wound material is then cut from the mandrel, rolled out flat and consolidated under loads of pressure and temperature, or the layup by hand of uniaxial prepreg tape or fiber tow, or any of the generally known and widely used methods for constructing these types of materials.

In a next step illustrated by block 88, the values for the Young's modulus and shear modulus of the preselected composite are calculated using the selected filament type and critical dimensions and selected matrix type. The Young's modulus and shear modulus may be calculated in any manner known to those skilled in the art, such as by the finite element analysis of the preferred embodiment.

As shown by block 90, and in a next step, either an upper or lower bound for the transverse stiffness, B, of the preselected composite is calculated using these values for Young's modulus and shear modulus. The choice of whether to calculate the upper or lower bound is dependent on the geometry of the component into which the composite is formed. More particularly the choice between calculation of the upper or lower bound is dependent upon the geometry of the components' cross section in a plane transverse to the direction of the filaments. For components having such a transverse cross section whose outline forms at least one angular break, equation (8) for the lower bound is to be chosen. (For example, calculation of the lower bound is to be chosen for a rectangular outline of cross section, which has four corners, or angular breaks.) For components having a transverse section whose outline is curvilinear in its entirety, equation (7) for the upper bound is to be chosen. (For example, calculation of upper bound is to be chosen for a circular outline of cross section, which is curvilinear, that is without any angular break).

As shown by block 92, and in the next step, critical stress, $P_c$, of the preselected composite is calculated using the one or the other of either the upper or lower bound for the transverse stiffness, B, which has been calculated in step 90.

It has been found that continuous filament reinforced composites fabricated in accordance with the present invention are free from microbuckling for loads below the range of loads established by the upper and lower bounds and in such a way as to exhibit a high degree of confidence in their load-bearing performance. To further insure the operational performance of the composites fabricated in accordance with the present invention, a safety factor, for example, 25%, could be built into the critical loads.

Many modifications of the presently disclosed invention will become apparent to those skilled in the art without departing from the scope of the appended claims.

What is claimed is:

1. A method for the fabrication of a continuous filament reinforced composite free from microbuckling deformation up to a predetermined load, comprising:

selecting a filament type;
for the selected filament type, selecting a filament length and thickness dimension;
selecting a matrix type;
controllably embedding filaments of said selected type into the selected matrix with the filaments in generally parallel aligned relationship to a filament alignment reference direction and in generally uniform spaced relation to one another, to fabricate a selected continuous filament reinforced composite;
calculating values for the selected continuous filament reinforced composite of its shear modulus and its Young's modulus of elasticity;
calculating using said values of the shear modulus and Young's modulus a value of transverse shear stiffness for the selected continuous filament reinforced composite; and
calculating using the value of the traverse shear stiffness a value of critical load below which the selected continuous filament reinforced composite is free from microbuckling deformations;
wherein the selected composite forms a structural member having a cross section in a plane transverse to said filament alignment reference direction whose outline is shaped to form at least one angular break, said value of transverse stiffness for the selected composite being calculated employing the relationship, $$B = \delta^{-1} = \left[ \frac{\frac{E_c}{E_c + 2G_c} \cdot \frac{t}{2}}{E_c} \right]^{-1}$$

which relationship is applicable to a normalized fiber/matrix continuum cell employing normalization factors $P=1$ and $A=1$ where P is stress load and A is cell area and further employing a normalization assumption that t is controlled by fiber diameter and fiber volume, and where B is transverse stiffness, $\delta$ is deflection in a direction transverse to the direction of the stress load, $E_c$ is Young's modulus for the composite, $G_c$ is shear modulus for the composite and t is test thickness in terms of a selected one or an other of spacial expanse or number of cells.

2. The invention of claim 1, wherein said controllably embedding step is accomplished by the steps of:
wet winding a uniaxial composite on a cylindrical mandrel;
cutting said wound uniaxial composite from said cylindrical mandrel;
rolling out flat said wound uniaxial composite; and
consolidating said wound uniaxial composite under loads of pressure and temperature.

3. The invention of claim 1, wherein values for shear modulus and Young's modulus of elasticity for the selected composite are calculated employing an analytical model representative of a discretized mesh of a composite unit cell subjected to plane strain elements and employing a finite element type of analysis to calculate said values in relation to said analytical model.

4. The invention of claim 1, wherein the value of critical load is calculated employing the relationship, $$P_c = \frac{n^2 E_f I_f}{L^2} \left[ n^2 + \frac{BL^4}{n^2 \pi^4 E_f I_f} \right]$$

which is applicable to the failure mode of generally sinuous compressive microbuckling deformation when a uniaxial compressive stress load is applied to said selected composite with the compressive forces acting in directions parallel to said filament alignment reference direction, and where $P_c$ is critical load value, n is the number of half wavelengths of sinusoidal buckling that occur within the composite along said filament alignment reference direction, $E_f$ is Young's modulus for the filament, L is said length of the filaments, B is the transverse stiffness of the selected composite, and $I_f$ is the moment of inertia of the filament.

5. The invention of claim 1, wherein said selected filament type is selected to be of aromatic polyamide.

6. The invention of claim 1, wherein said selected filament type is selected to be of carbon.

7. The invention of claim 1, wherein said selected filament type is selected to be of fiberglass.

8. The invention of claim 1, wherein said selected matrix type is selected to be of epoxy.

9. The invention of claim 1, wherein said selected matrix type is selected to be of thermoplastic.

10. The invention of claim 1, wherein said selected matrix type is selected to be of thermosetting material.

11. A method for the fabrication of a continuous filament reinforced composite free from microbuckling deformation up to a predetermined load, comprising:
selecting a filament type;
for the selected filament type, selecting a filament length and thickness dimension;
selecting a matrix type;
controllably embedding filaments of said selected type into the selected matrix with the filaments in generally parallel aligned relationship to a filament alignment reference direction and in generally uniform spaced relation to one another, to fabricate a selected continuous filament reinforced composite;
calculating values for the selected continuous filament reinforced composite of its shear modulus and its Young's modulus of elasticity;
calculating using said values of the shear modulus and Young's modulus a value of transverse shear stiffness for the selected continuous filament reinforced composite;
calculating using the value of the transverse shear stiffness a value of critical load below which the selected continuous filament reinforce composite is free from microbuckling deformation; and
wherein the selected composite forms a structural member having a cross section in a plane transverse to said filament alignment reference direction whose outline is curvilinear in its entirety, said value of transverse stiffness for the selected composite being calculated employing the relationship $$B = \delta^{-1} = \left[ \frac{\frac{E_c}{E_c + 4G_c} \cdot \frac{t}{2}}{E_c} \right]^{-1}$$

which relationship is applicable to a normalized fiber/matrix continuous cell employing normalization factors P=1 and A=1, where P is stress load and A is cell area and employing a normalization assumption that t is controlled by fiber diameter and fiber volume, and where B is transverse stiffness, $\delta$ is deflection in a direction transverse to the direction of the stress load, $E_c$ is Young's modulus for the composite, $G_c$ is shear modulus for the composite, and t is test thickness in terms of a selected one or an other of spacial expanse or number of cells.

12. The invention of claim 11, wherein said controllably embedding step is accomplished by the steps of:
    wet winding a uniaxial composite on a cylindrical mandrel;
    cutting said wound uniaxial composite from said cylindrical mandrel;
    rolling out flat said wound uniaxial composite; and
    consolidating said wound uniaxial composite under loads of pressure and temperature.

13. The invention of claim 11, wherein values for shear modulus and Young's modulus of elasticity for the selected composite are calculated employing an analytical model representative of a discretized mesh of a composite unit cell subjected to plane strain elements and employing a finite element type of analysis to calculate said values in relation to said analytical model.

14. The invention of claim 11, wherein the value of critical load is calculated employing the relationship, $$P_c = \frac{n^2 E_f I_f}{L^2} \left[ n^2 + \frac{BL^4}{n^2 \pi^4 E_f I_f} \right]$$

which is applicable to the failure mode of generally sinuous compressive microbuckling deformation when a uniaxial compressive stress load is applied to said selected composite with the compressive forces acting in directions parallel to said filament alignment reference direction, and where $P_c$ is critical load value, n is the number of half wavelengths of sinusoidal buckling that occur within the composite along said filament alignment reference direction, $E_f$ is Young's modulus for the filament, L is said length of the filaments, B is the transverse stiffness of the selected composite, and $L_f$ is the moment of inertia of the filament.

15. The invention of claim 11, wherein said selected filament type is selected to be of aromatic polyamide.

16. The invention of claim 11, wherein said selected filament type is selected to be of carbon.

17. The invention of claim 11, wherein said selected filament type is selected to be of fiberglass.

18. The invention of claim 11, wherein said selected matrix type is selected to be of epoxy.

19. The invention of claim 11, wherein said selected matrix type is selected to be of thermoplastic.

20. The invention of claim 11, wherein said selected matrix type is selected to be of thermosetting material.

* * * * *